US00PP10263P

United States Patent [19]

Brown

[11] Patent Number: Plant 10,263

[45] Date of Patent: Feb. 24, 1998

[54] AGLAONEMA PLANT NAMED 'ROYAL QUEEN'

[75] Inventor: B. Frank Brown, Valkaria, Fla.

[73] Assignee: Sunshine Foliage World, Zolfo Springs, Fla.

[21] Appl. No.: 754,303

[22] Filed: Nov. 21, 1996

[51] Int. Cl.[6] ..... A01H 5/00

[52] U.S. Cl. ..... Plt./88.1

[58] Field of Search ..... Plt./88.1

*Primary Examiner*—James R. Feyrer
*Attorney, Agent, or Firm*—C. A. Whealy

[57] ABSTRACT

A new and distinct cultivar of Aglaonema named 'Royal Queen' particularly characterized by its large spreading growth habit and its large tri-color leaves which are abundantly marked with two shades of silver green.

2 Drawing Sheets

The present invention relates to a new and distinct cultivar of Aglaonema plant, botanically known as *Aglaonema hybrida*, and hereinafter referred to by the cultivar name Royal Queen.

The new cultivar is a product of a planned breeding program conducted by the inventor in Valkaria, Fla. The new cultivar originated from a cross made by the inventor in May, 1986, between the nonpatented *Aglaonema nitidum* f. nitidum as the female, or seed, parent with the species *Aglaonema panayensis*. The cultivar Royal Queen was discovered and selected by the inventor in August, 1989, as a plant within the progeny of the stated cross in a controlled environment in Valkaria, Fla.

Asexual propagation of the new cultivar at Valkaria, Fla., has shown that the unique features of this new Aglaonema plant are stable and reproduced true to type in successive generations of asexual propagation.

The new Aglaonema has not been observed under all possible environmental conditions. The phenotype may vary somewhat with variations in environment such as temperature, light intensity and fertilizer rate, without, however, any variance in genotype. The following observations, measurements and comparisons describe plants grown in Zolfo Springs, Fla., under a polypropylene-covered shadehouse and conditions which closely approximate those used in horticultural practice.

The following traits have been repeatedly observed and are determined to be the unique characteristics of 'Royal Queen'. These characteristics in combination distinguish 'Royal Queen' as a new and distinct cultivar:

1. Plants of the new Aglaonema are large and spreading in growth habit.

2. The leaves of the new Aglaonema are relatively large.

3. The abaxial leaf surfaces of the new Aglaonema are abundantly marked with three shades of green. The midrib and leaf margin are dark green and chevrons of two shades of silver green comprise a large area of the leaf surface.

Plants of the new Aglaonema can be compared to plants of the nonpatented Aglaonema cultivar Silver Queen which have a similar leaf color pattern. However, leaves of plants of the new Aglaonema are much more abundantly marked with three shades of green. In addition, plants of the new Aglaonema have much larger leaves and grow considerably taller and wider than plants of Silver Queen.

The accompanying colored photographs illustrate the overall appearance of the new cultivar, showing the colors as true as it is reasonably possible to obtain in colored reproductions of this type.

The first photograph comprises a top perspective view of a typical single plant of 'Royal Queen' in a 26-cm container about 18 months after planting a single four-leaf cutting.

The second photograph comprises a close-up view of the abaxial (left) and adaxial (right) surfaces of a mature leaf and illustrates the detail of the leaf color pattern. Leaf colors in the photographs may appear different from the actual colors due to light reflectance.

In the following description, color references are made to The Royal Horticultural Society Colour Chart except where general terms of ordinary dictionary significance are used.

Botanical classification: *Aglaonema hybida* cultivar Royal Queen.

Parentage:

*Seed or female parent.*—*Aglaonema nitidum* f. nitidum (not patented).

*Pollen or male parent.*—*Aglaonema panayensis.*

Propagation:

Asexual propagation by division or tissue culture.

Plant description:

*Plant shape.*—Tall and wide, outwardly spreading and symmetrical.

*Growth habit.*—Relatively erect when young, becoming more outwardly spreading as leaves develop.

*Plant size.*—Height: Soil surface to top of leaf canopy: Approximately 68 to 75 cm. Soil surface to junction of the petioles of the last two unrolled leaves: Approximately 30 to 36 cm. Width: Approximately 100 to 111 cm.

*Root description.*—Thick white roots with fine laterals.

*Stem description.*—Tall and upright. Diameter, 5 cm above the soil surface: Approximately 2.2 to 2.5 cm. Internode length, 3 cm above the soil surface: Approximately 1.8 to 2.1 cm. Color: 147A/147B with areas of 164C/164D.

*Petiole description.*—The following description is based on the fourth expanded leaf from the apex. Growth pattern: The petiole has fleshy edges extending from the midrib that are referred to as wings. Wings extend from the base of the petiole to approximately 1.2 to 4 cm below the base of the leaf. The wings are about 5 to 8 mm wide midway from the petiole base to the wing apex. The wing apex is acute. The petiole follows the stem axis but diverges from the axis about 14 to 16.5 cm from the leaf base, forming a horizontal distance from the vertical axis of the stem to the leaf base of approximately 8.5 to 10.2 cm. Dimensions: The petiole is straight from its base to the tip of the wings, and often curved between the tip of the wings and the base of the leaf. The petiole is approximately 5 to 7 mm in diameter midway between the wing apex and the base of the leaf. The petiole is approximately 18.5 to 20.7 cm in length from its base to the base of the leaf. Color: Petiole wings: 137A/144A with spots and streaks of 193A. Midrib: Greener than 193A with occasional spots and streaks of 144A.

*Axillary breaks.*—There are approximately 5 axillary breaks with at least one leaf expanded. First leaves will show true color and color pattern.

*Leaf description.*—Growth Pattern: The leaf is ovate with an acuminate apex and an acute base. The margin is entire. The leaf is oriented parallel to the stem axis at the time of full unrolling, changing to approximately 50 to 60 degrees from vertical stem axis as more leaves unroll above it. The midrib is curved downward over the length of the leaf. The leaf blade is flat from the midrib to the margin and often slightly wavy along the margin. Dimensions: For the pot size and growing time indicated, the largest leaves are approximately 36 to 39.1 cm long and approximately 11 to 13.7 cm wide. Average sized leaves are approximately 32.2 to 25.2 cm long and approximately 9.9 to 12.1 cm wide. The leaf blade is relatively thick and leathery in texture with a matte to slightly glossy surface. Midrib: The midrib is thick and prominent, recessed on the abaxial leaf surface and prominent on the adaxial surface. Primary veins: The primary veins are sunken into the abaxial surface and slightly prominent on the adaxial surface. The primary veins are the same color as the tissue surrounding them. The leaf blade is convex between the primary veins. Color pattern: The abaxial leaf surfaces are marked with three shades of green. The leaf margin and midrib are dark green. Chevrons of dark green extend from the midrib toward the margin. Chevrons consisting of two shades of silver green radiate out from the midrib toward the leaf margin and occupy much of the leaf surface. The adaxial leaf surface is medium green with irregular shaped pale green blotches. Color: Mature leaf, abaxial surface: Leaf margins and dark green chevrons: 147A. Silver green central area: 191A. Dark silver green chevrons: 189A. Midrib: 147A with occasional streaks of 191A. Mature leaf, adaxial surface: Base color: 147A/147B with pale green blotches of 147C. Midrib: 147D with streaks 146C. Newly opened leaf, abaxial surface: Leaf margins and dark green chevrons: 147A. Silver green central area: 191C. Dark silver green chevrons: 191A. Midrib: 137A with streaks of 191C. Newly opened leaf, adaxial surface: Base color: 147B with pale green blotches of 147C. Midrib: 147D with streaks of 146D.

*Inflorescence.*—Typical of Aglaonema, no commercial significance.

GENERAL OBSERVATIONS

Aglaonema 'Royal Queen' is a large growing variety having large tri-color leaves with abundant silver green markings. These characteristics in combination make 'Royal Queen' a unique and distinct new cultivar.

It is claimed:

1. A new and distinct cultivar of Aglaonema plant named 'Royal Queen', as illustrated and described.

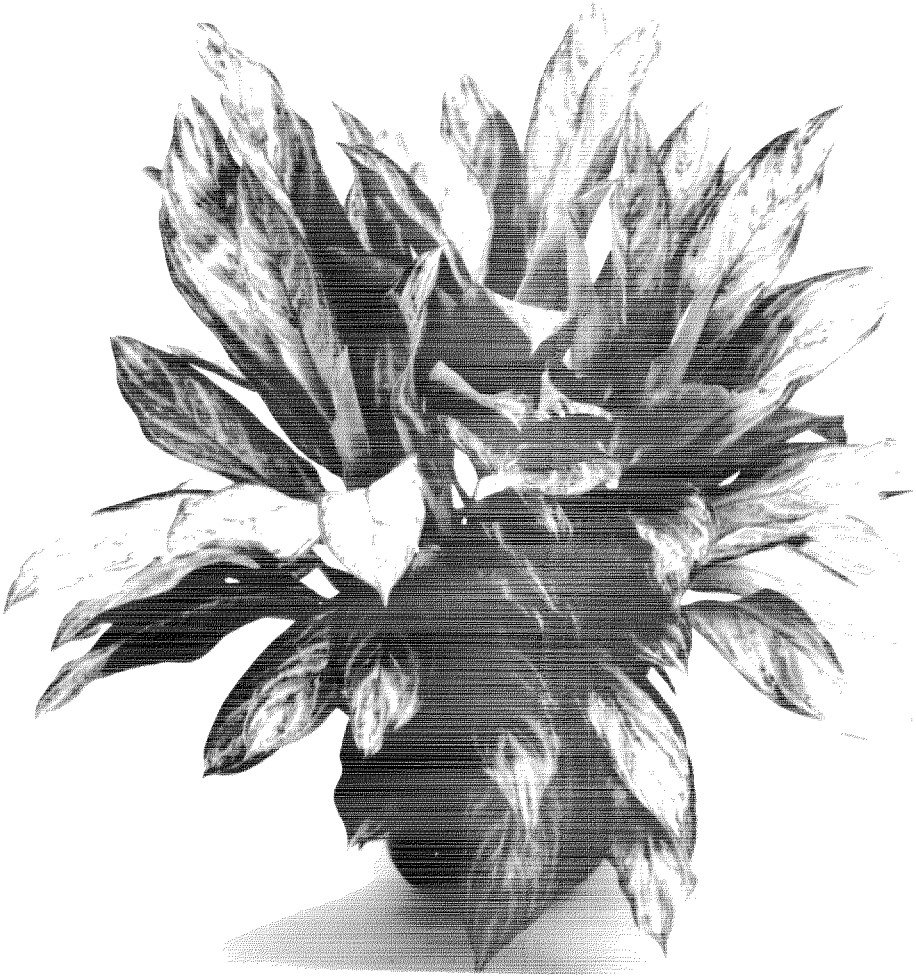

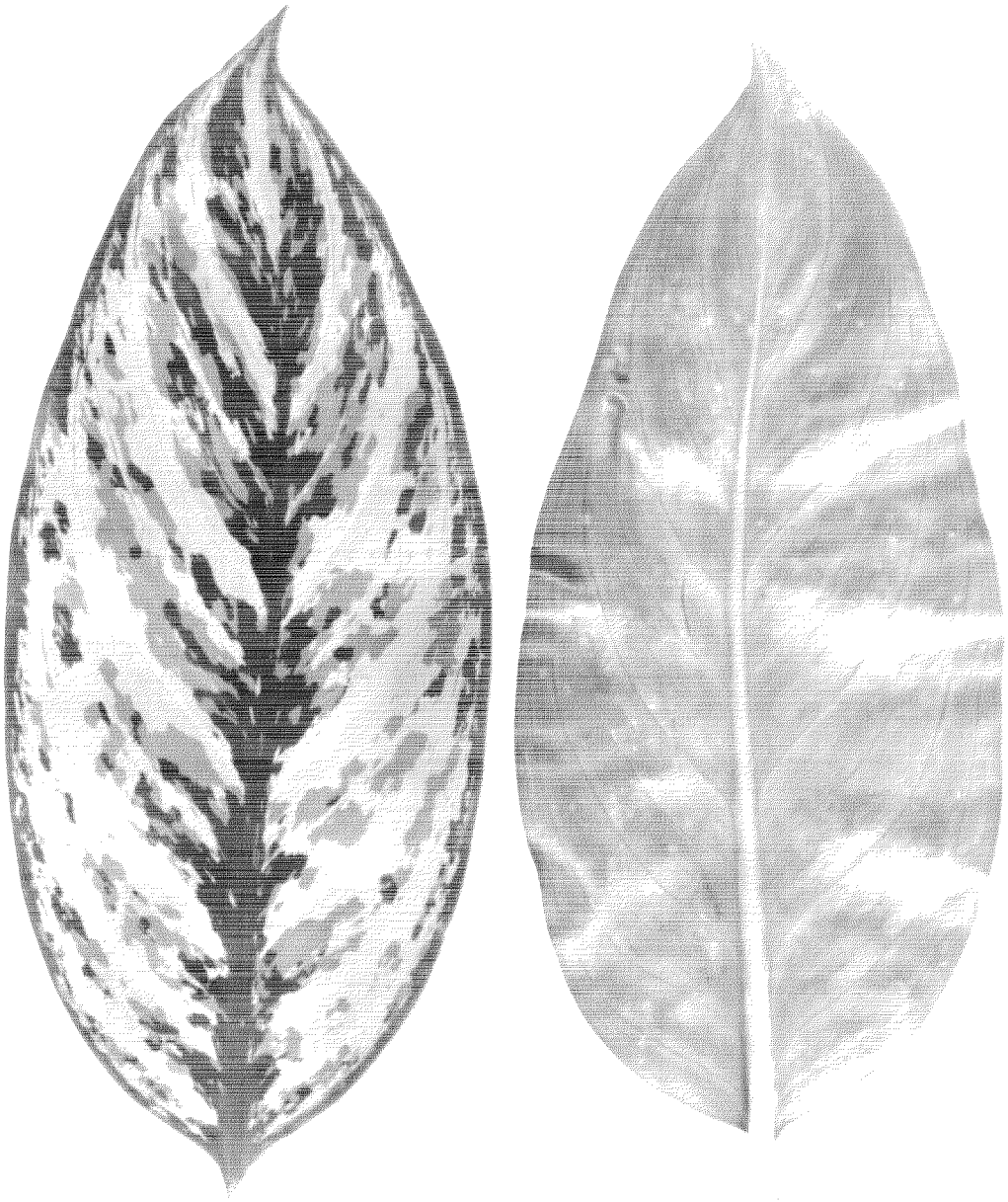

* * * * *